United States Patent [19]

Curtis

[11] Patent Number: 4,888,995
[45] Date of Patent: Dec. 26, 1989

[54] TEST SPECIMEN GRIP APPARATUS

[76] Inventor: John M. Curtis, 1500 Glenmar St., Natrona Heights, Pa. 15065

[21] Appl. No.: 269,357

[22] Filed: Nov. 10, 1988

[51] Int. Cl.$^4$ .............................................. G01N 3/02
[52] U.S. Cl. ...................................................... 73/859
[58] Field of Search ................. 73/856, 857, 859, 860; 269/25; 279/60

[56] References Cited

U.S. PATENT DOCUMENTS 2,702,929 3/1955 Laddon et al. .................. 73/859 X
4,662,229 5/1987 Curtis .................................... 73/859

*Primary Examiner*—Jerry W. Myracle
*Attorney, Agent, or Firm*—Lawrence G. Zurawsky; Thomas F. Shanahan

[57] ABSTRACT

Improvements in test specimen grip apparatus for tensile stress testing machines includes replaceable grip inserts that are able to accommodate wider than usual test specimens, particularly textile test specimens. The specimen grip means or grip inserts are threadedly retained on and may be substantially wider than their supporting jaw members. The grip housing, moreover, is provided with apertures for access to the threaded retainers for ease of grip insert removal and replacement. In addition, fluid actuation is preferably provided for the jaw members of the improved grip apparatus and a thumb screw is also disclosed for temporarily locking the jaw members in a selected open position, when mounting test specimens or removing and/or replacing grip inserts.

23 Claims, 2 Drawing Sheets

TEST SPECIMEN GRIP APPARATUS

BACKGROUND OF THE INVENTION

1. Field of the Invention

The invention relates to improvements in test specimen grip apparatus for testing machines and, more specifically, to improvements in grip apparatus for tensile stress testing machines. The grip apparatus disclosed is capable of holding test specimens, such as textile test specimens, that are wider than usual dog bone specimens or the like and, in addition, is provided with desirable fluid actuation, a thumb screw lock for its jaw members and an arrangement whereby grip inserts can be rapidly and easily removed and replaced.

2. Description of the Prior Art

This invention is an improvement in wedge grips for testing machines and, in particular in the grip apparatus disclosed in applicant's U.S. Pat. No. 4,662,229, issued May 5, 1987, entitled Grip Assembly, the disclosure of which is incorporated herein by reference. Disclosed in applicant's said prior patent is test specimen grip apparatus for use with universal type testing machines. The grip apparatus disclosed includes a grip housing having a connecting end adapted for securing the housing to tensile stress testing apparatus and a test specimen receiving end opposite the connecting end of the housing. A pair of passages extend through the connecting end of the housing and converge toward the housing's receiving end. A cavity in the housing is in operative communication with the pair of passages and with the receiving end of the housing and is adapted for receiving one end of a test specimen within the grip housing. A grip bar is slidable mounted in each of the converging passages and each grip bar extends above the connecting end of the housing. Moreover, each grip bar is provided with specimen grip means carried on its lower end, the grip means being opposed and being adapted to compressively engage oppose surfaces of a test specimen, whereby application of tensile stress to the test specimen increases the compressive engagement of the grip means with the test specimen.

Notwithstanding the patentable features and advantages of the foregoing grip assembly over those known in the prior art, applicant's prior grip assembly was not well suited for tensile testing textile materials, particularly as the tensile test specimen increased in width. A review of the prior patents disclosed or cited in applicant's U.S. Pat. No. 4,662,229, including U.S. Pat. Nos. 1,510,896; 2,419,711; 2,447,660; 2,537,322; 2,613,941; 2,676,381; 3,224,259 and 3,403,549, the disclosures of which are incorporated herein by reference, provided no structure by which textile test specimens of varying widths, such as up to at least twelve (12) inches or more in width, could be accommodated for tensile testing. Moreover, a review of additional patents disclosed in U.S. Pat. No. 4,662,229, including Canadian Pat. No. 446,096 and Soviet Union Pat. No. 800,797, the disclosures of which are also incorporated by reference, was similarly of no avail in providing or suggesting a suitable grip structure for tensile testing textile specimens of such widths as heretofore stated.

Accordingly, there remained a need for a grip apparatus for use with conventional tensile stress testing devices that was readily adaptable for use with test specimens of varying widths, including textile test specimens of up to at least twelve (12) inches or more in width. Moreover, the need for such grip apparatus included the further need for an apparatus which permits easy and rapid removal and replacement of test specimens, as well as easy and rapid removal and replacement of the specimen grip members without removal of the grip apparatus from the test device and without substantial disassembly of the grip apparatus.

SUMMARY OF THE INVENTION

In accordance with the present invention, there is provided a novel and improved grip apparatus for tensile stress testing machines that includes replaceable grip inserts that are able to accommodate wider than usual test specimens, particularly textile test specimens. The specimen grip means or grip inserts are threadedly retained on and may be substantially wider than their supporting jaw members. The grip housing, moreover, is provided with apertures for access to the threaded retainers for ease of grip insert removal and replacement. In addition, fluid actuation is preferably provided for the jaw members of the improved grip apparatus and a thumb screw is also disclosed for temporarily locking the jaw members in a selected open position, when mounting test specimens or removing and/or replacing grip inserts.

Description of the Preferred Embodiment

The construction and operation of conventional tensile stress testing apparatus, such as universal type testing machines, is well known and is suitably described in applicant's U.S. Pat. No. 4,662,229. As therein disclosed, the stress testing apparatus is generally comprised of a top or cross member and a base member or platen. A grip apparatus, such as the grip apparatus of the present invention, is attached by its connecting end to the top member of the testing apparatus and an identical grip apparatus is attached by its connecting end to the base member of the testing apparatus. Opposite ends of a test specimen are received and secured in the opposed, specimen receiving ends of the grips for testing. Stress measuring means, such as a load cell, is employed with the testing apparatus and may be interposed between one of the grips, such as the top grip, and its attached machine support. With such an arrangement, tensile stress is applied directly through the load cell to the test specimen, and, stress measurements, of the amount of tensile stress so applied, are recorded simultaneously by a device attached to the load cell.

Figure 1:
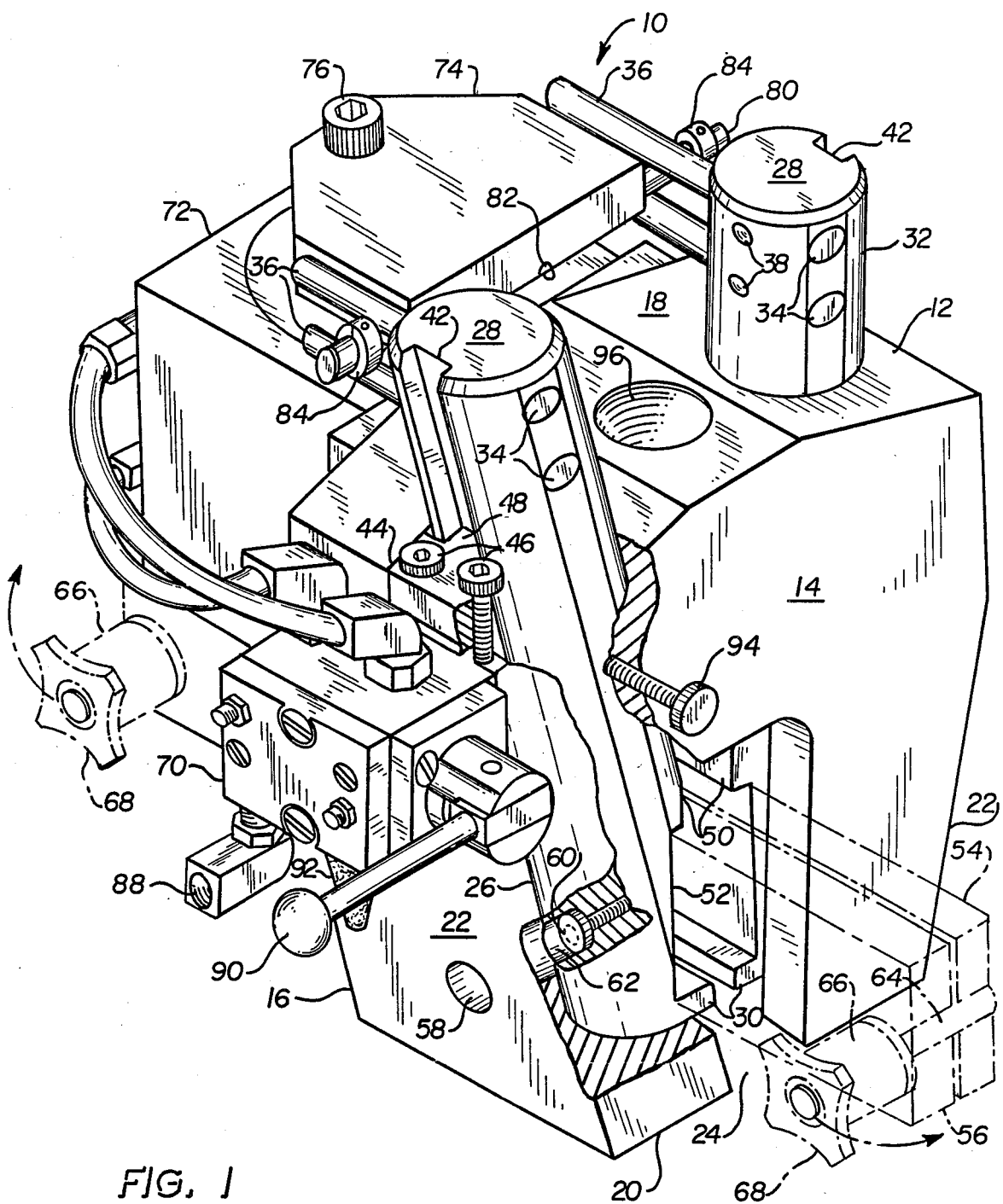
FIG. 1 is a perspective of a preferred embodiment of the grip apparatus if this invention with portions broken away to clearly illustrate certain interior details.
Figure 2:
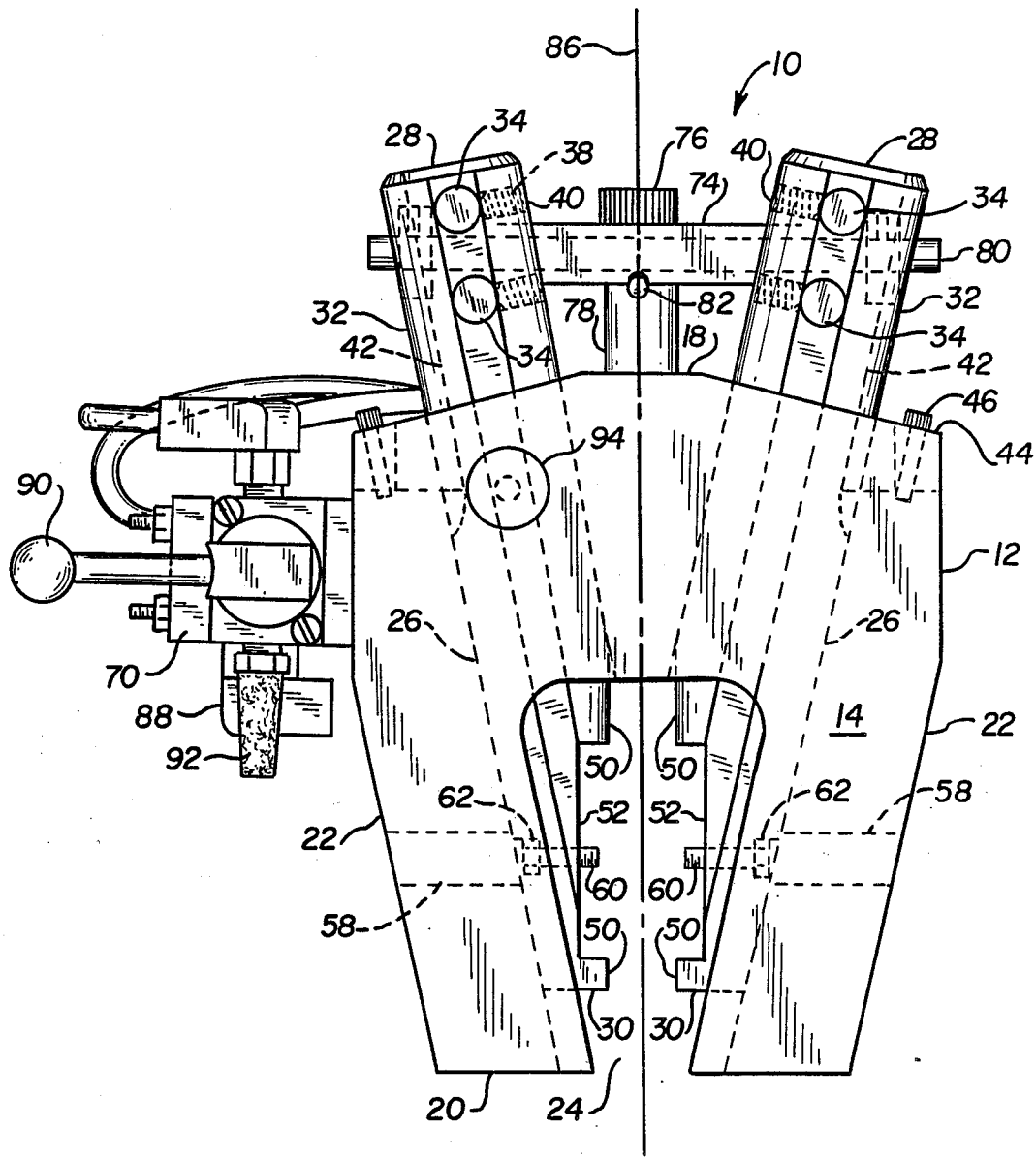
FIG. 2 is a front elevation of the grip apparatus of FIG. 1.

Shown in FIGS. 1 and 2 is a preferred grip apparatus of this invention. The preferred grip apparatus is indicated generally by the reference numeral 10 and comprises a generally U-shaped housing 12 having a front surface 14, a rear surface 16, a connecting end surface 18, a specimen receiving end surface 20, and opposed side surfaces 22. In a preferred embodiment of this invention, housing 12 is of unitary construction consisting of a single piece of material. Housing 12 can be constructed of any suitable material that provides the strength and rigidity required for the particular range of tensile stress to be applied to a selected work piece or test specimen. For example, for high stress use, housing 12 can be constructed of steel or other suitable metal. For low stress use for testing materials having low tensile strength, such as thin gauge wire or plastic materials, housing 12 can be constructed of plastic or other strong, rigid, non-metallic materials. In a preferred embodiment of this invention, for use with high tensile strength materials having tensile strength in excess of thirty thousand (30,000) pounds per square inch, housing 12 has been constructed of aluminum.

With particular reference to FIG. 2, an inwardly opening, generally V-shaped cavity 24 extends from the specimen receiving end surface 20 of the housing 12 through a portion of the housing 12 and also extends from the front surface 14 to the rear surface 16 of the housing. A pair of bores or passages 26 extend from the connecting end surface 18 of housing 12, through housing 12, to the specimen receiving end surface 20. Bores or passages 26 mutually converge and open into cavity 14, as bores or passages 26 extend toward specimen receiving end surface 20 of housing 12. In a preferred embodiment of this invention, bores or passages 26 are circular in transverse cross-section; however, in other embodiments of this invention, bores or passages 26 may be either polygonal or of curved, non-round transverse cross-section.

In each of the bores or passages 26, there is slidable mounted a grip bar 28, which extends downwardly through housing 12 and has a bottom surface 30 which may be flush with the specimen receiving end surface 20 of housing 12. An upper portion 32 of grip bar 28 extends beyond connecting end surface 18 of housing 12. A pair of mutually spaced aligned holes 34 extend through upper portion 32 of grip bar 28. Each hole 34 contains a pin 36, extending outwardly from grip bar 28 toward rear surface 16 of housing 12. Laterally adjacent and normal to each hole 34 and each pin 36, a threaded bore 38 extends through grip bars 28 into holes 34 and secures a threaded set screw 40 which abuts pins 36 and secures pins in place. The function of pins 36 is discussed more fully below.

The peripheral transverse configuration of grip bar 28 conforms to the shape of the transverse cross-section of bore or passage 26 in a manner adapted to provide a close tolerance, readily slidable fit between the surfaces of bore or passage 26 and grip bar 28, while preventing damage to those surfaces while the grip apparatus is in use. In a preferred embodiment of this invention, grip bar 28 is cylindrical and conforms to a circular transverse cross-section of bore or passage 26. In another embodiment of this invention, the transverse cross-section of grip bar 28 can be polygonal or of a non-round, curved configuration. In all instances, the cross-sectional configuration of grip bar 28 conforms to the cross-sectional configuration of bore or passage 26.

A groove 42 is formed in the side of grip bar 28, opposite threaded bores 38, and extends a portion of the length of grip bar 28 adjacent the side surface 22 of housing 12. A key or guide 44 is secured by fasteners 46 to the connecting end surface 18 of housing 12 adjacent groove 42. A forwardly projecting portion 48 of key or guide 44 extends into groove 42 to enable proper slidable alignment of grip bar 28 and to prevent turning of grip bar 28 when grip apparatus 10 is in use. Of course, key or guide 44 and groove 42 may be omitted when grip bars 28 and bores or passages 26 have a polygonal transverse cross-section, or other configuration, that prevents turning of the grip bars 26 in use.

As shown particularly in FIG. 2, each of the grip bars 26 has a planar surface 50 formed on the lower portion of grip bar 28. A rectangular notch, seat or recess 52 is formed in the planar surface 50 of each grip bar 26 to receive and secure laterally opposed grip jaw inserts 54 and 56 in grip bars 28.

Grip jaw inserts 54 and 56, shown in chain line or phantom in FIG. 1, are typical of a set of such inserts that can be employed with textile test specimens in the practice of the present invention. As illustrated, jaw inserts 54 and 56 are wider than their respective supporting grip bars 28. For example, grip bars 28 may be of a width or diameter of about 1⅛ inches, whereas the grip jaw inserts 54 and 56, illustrated in FIG. 1, are about 9 inches wide × 1½ inches high × 11/32 inch deep. Obviously, none of the foregoing dimensions are intended to be critical. However, the preferred practice of one aspect of the invention is based on the premise that for textile test specimens or the like there is a need for, and, the invention provides, a grip apparatus in which the set of grip jaw inserts 54 and 56 are wider than the respective width of the supporting jaw members or grip bars 28. This difference in width may vary from a relatively moderate difference to a rather substantial difference, such as a ratio of 12:1 or more.

For the purpose of securing grip jaw inserts 54 and 56 to jaw members or grip bars 28 and, in addition, for ease of removal and replacement of such jaw inserts, there is provided an arrangement including bores or apertures 58 in housing 12 and recessed threaded retainers 60 received in and passing through countersunk holes 62 in grip bars 28. The threaded retainers 60 are secured in a threaded bore (not shown) located centrally in the grip inserts 54 and 56. Threaded retainers 60 are preferably of a type having an allen head. It will be understood that, by aligning threaded retainers 60 with apertures 58, grip inserts 54 and 56 can be easily installed, removed or replaced by use of an allen wrench inserted through apertures 58.

The finish provided on the specimen gripping surface of inserts 54 and 56 can be chosen to suit the particular material being tensile tested. Thus, the gripping surface can be cross-scored, serrated, in the nature of a sand paper finish or any other finish that is found to be desirable. It will also be noted that the grip inserts illustrated in FIG. 1 are shown to be provided on their extreme ends with a clamping arrangement comprising a threaded rod 64 pivotally mounted to one grip insert and a suitable locking nut 66. As will be understood, the grip inserts 54 and 56 are provided at their ends with a groove (not shown) to accommodate receiving threaded rod 64 therein. Also, as shown, locking nut 66 is preferably provided with a convenient hand wheel 68 for ease of tightening.

Grip bars 28 and grip jaw inserts 54 and 56, of the apparatus of this invention, can be made of any suitable rigid material having sufficient strength to withstand the range of tensile stress to be applied to a particular work piece or test specimen. In a preferred embodiment of this invention, grip bars 28 and grip jaw inserts 54 and 56 are made of steel.

A further improvement in the test specimen grip apparatus 10 of this invention resides in the provision of fluid actuation means for grip bars 28 and, accordingly, for the grip jaw inserts 54 and 56 that are secured thereon. In this connection, there is mounted on housing 12 a fluid control valve 70 and a double acting, piston-cylinder assembly 72. The center line of piston-cylinder assembly 72 is parallel to and rearwardly spaced from the central longitudinal axis 86 of housing 12, in a plane that bisects housing 12. One end of a drive plate 74 is secured by an allen head screw 76 to the upper end of piston rod extension 78, of the piston cylinder assembly 72. Drive plate 74 is provided with a transverse pin 80 secured by a set screw 82 in a bore (not shown) in the opposite end of drive plate 74 from its attachment to piston rod extension 78. Drive plate pin 80 bridges and loosely nests between the pair of mutually spaced aligned pins 36 extending outwardly from grip bars 28 toward rear surface 16 of housing 12. A collar 84 is secured by set screws at a selected position near each end of drive plate pin 80. The position of collars 84 on drive plate pin 80 sets and determines the length of stroke of the piston portion of piston-cylinder assembly 72.

In operation, a fluid, which may be a pneumatic or hydraulic fluid but in the preferred embodiment shown in compressed air, is introduced into valve inlet fitting 88 of fluid control valve 70. Movement of valve control hand lever 90 to a first position allows the compressed air to pass through valve 70 to the lower end of piston-cylinder assembly 72, driving the piston and the piston rod extension 78 upward and, through the interaction of drive plate pin 80 with grip bar pins 36, to raise the grip bars 28 to their upper or open operating position, for either mounting or removing a test specimen from grip apparatus 10. Retained air in the upper end of piston-cylinder assembly 72 escapes through a sintered metal exhaust filter 92, shown mounted on fluid control valve 70. Conversely, movement of the valve control hand lever 90 to a second position allows the compressed air to pass through valve 70 to the upper end of piston-cylinder assembly 72, simultaneously closing off the exhaust and driving the piston and the piston rod extension 78 downward, and, through the interaction of drive plate pin 80 with grip bar pins 36, to lower the grip bars 28 to their lower or closed operating position for tensile testing of a test specimen.

An example of a suitable valve 70, for use in with this invention, is a MAC 1100A Series valve, available from MAC ® Valves, Inc., P.O. Box 111, 30569 Beck Road, Wixam, Mich. 48096 or their distributors. An example of a piston-cylinder assembly 72, that has been found particularly satisfactory, is a HUSKY TM Square Base Mount Cylinder B158×112, available from Compact Air Products, Inc., P.O. Box 176, Rt. 1, Hwy. 123, Westminster, SC 29693.

Also, shown in FIGS. 1 and 2, is a convenient thumb screw feature of this invention wherein a thumb screw 94 is threadedly secured in the front surface 14 of housing 12, directly opposite to one of the grip bars 28, such that, by tightening the thumb screw 94, it bears against its associated grip bar 28. Thumb screw 94 is useful with grip apparatus, such as the grip apparatus disclosed in applicant's U.S. Pat. No. 4,662,229 or the grip apparatus disclosed herein, for the purpose of locking interconnected grip bars 28 in a selected open position, such as when removing and replacing grip inserts 54 and 56.

A threaded hole 96, in the connecting end surface 18 of housing 12, is provided to connect grip apparatus 10 to tensile testing machines. Moreover, hole 96 is adapted to receive a connector (not shown) having both external and internal threads for the purpose of adapting grip apparatus 10 to certain of the testing machines. In any event, hole 96, or hole 96 and said connector-adaptor, or other suitable connecting means can be used to enable connection of grip apparatus 10 to any type of existing tensile stress testing apparatus.

Maintenance of a suitable angle formed between grip bars 28 is useful in providing a grip apparatus of exceptional strength and gripping force, even when the housing is constructed of light weight materials, such as aluminum. One convenient manner of describing that angle is the angle formed between the central longitudinal axis of bores of passages 26 that provide required wedging surfaces and the central longitudinal axis 86 of housing 12. A suitable range for that angle in the apparatus of this invention is from approximately 10 degrees to approximately 40 degrees. In a preferred embodiment of this invention, that angle is 15 degrees.

The apparatus of the invention provides a wedge grip that can be used with new or previously known tensile stress testing apparatus to test low, medium or high tensile strength materials without risk of failure of the grip apparatus. The grip apparatus of this invention is of relatively simple and inexpensive construction, can be made of relatively light weight materials, and can be so constructed as to have a relatively low gross weight for the grip apparatus. The apparatus of this invention provides the further advantage of permitting easy and rapid removal and replacement of the grip jaw inserts without removal of the grip apparatus from the test device and without substantial disassembly of the grip apparatus. The apparatus is particularly useful for tensile testing textile materials.

Although the apparatus of this invention has been described with respect to its use with tensile stress testing apparatus, the apparatus of the invention can be used with other types of material strength or stress testing apparatus, such as testing apparatus used to test resistance to torsion or bending.

According to the provisions of the patent statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

Therefore, I claim:

1. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a pair of passages extending through said connecting end of said housing and converging toward said receiving end of said housing, a cavity adapted for receiving one end of a test specimen within said housing, said cavity being in operative communication with said pair of passages, and a pair of grip bars, one of said grip bars being slidably mounted in one of said passages and the other of said grip bars being slidably mounted in the other of said passages, each of said grip bars extending above said connecting end of said housing and each of said grip bars having grip means carried on its lower end, said grip means being opposed and being adapted to compressively engage opposed surface of a test specimen, whereby application of tensile stress to said test specimen increases the compressive engagement of said grip means with said test specimen, the improvement comprising, each of said opposed grip means being constructed and arranged to extend transversely of said grip bars a distance greater than the width of said grip bars.

2. Test specimen grip apparatus according to claim 1 which further includes fluid actuation means operatively connected to said grip bars to selectively slide said grip bars between an open position and a closed position.

3. Test specimen grip apparatus according to claim 2 which further includes locking means carried on said housing for locking said grip bars in a selected open position and wherein said grip means are supported on said grip bars by threaded retainers passing through said grip bars and said housing includes aperture means for access to said threaded retainers.

4. Test specimen grip apparatus according to claim 1 which further includes locking means carried on said housing for locking said grip bars in a selected open position.

5. Test specimen grip apparatus according to claim 1 wherein said grip means are supported on said grip bars by threaded retainers passing through said grip bars and said housing includes aperture means for access to said threaded retainers.

6. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a pair of passages extending through said connecting end of said housing and converging toward said receiving end of said housing, a cavity adapted for receiving one end of a test specimen within said housing, said cavity being in operative communication with said pair of passages, and a pair of grip bars, one of said grip bars being slidably mounted in one of said passages and the other of said bars being slidably mounted in the other of said passages, each of said grip bars extending above said connecting end of said housing and each of said grip bars having grip means carried on its lower end, said grip means being opposed and being adapted to compressively engage opposed surfaces of a test specimen, whereby application of tensile stress to said test specimen increases the compressive engagement of said grip means with said test specimen, the improvement comprising,
fluid actuation means mounted on the exterior of said housing and operatively connected to said grip bars at a location outside of said housing to selectively slide said grip bars between an open position and a closed position.

7. Test specimen grip apparatus according to claim 6 which further includes locking means carried on said housing for locking said grip bars in a selected open position.

8. Test specimen grip apparatus according to claim 6 wherein said grip means are supported on said grip bars by threaded retainers passing through said grip bars and said housing includes aperture means for access to said threaded retainers.

9. In test specimen grip apparatus for use in the tensile stress testing apparatus wherein said grip apparatus includes a housing having a connecting end adapted for securing said housing to said tensile stress testing apparatus, a test specimen receiving end opposite said connecting end of said housing, a pair of passages extending through said connecting end of said housing and converging toward said receiving end of said housing, a cavity adapted for receiving one end of a test specimen within said housing, said cavity being in operative communication with said pair of passages, and a pair of grip bars, one of said grip bars being slidably mounted in one of said passages and the other of said grip bars being slidably mounted in the other of said passages, each of said grip bars extending above said connecting end of said housing and each of said grip bars having grip means carried on its lower end, said grip means being opposed and being adapted to compressively engage opposed surfaces of a test specimen, whereby application of tensile stress to said test specimen increases the compressive engagement of said grip means with said test specimen, the improvement comprising,
locking means carried on said housing for locking said grip bars in a selected open position.

10. Test specimen grip apparatus according to claim 9 wherein said grip means are supported on said grip bars by threaded retainers passing through said grip bars and said housing includes aperture means for access to said threaded retainers.

11. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a pair of passages extending through said connecting end of said housing and converging toward said receiving end of said housing, a cavity adapted for receiving one end of a test specimen within said housing, said cavity being operative communication with said pair of passages, and a pair of grip bars, one of said grip bars being slidably mounted in one of said passages and the other of said grip bars being slidably mounted in the other of said passages, each of said grip bars extending above said connecting end of said housing and each of said grip bars having grip means carried on its lower end, said grip means being opposed and being adapted to compressively engage opposed surfaces of a test specimen, whereby application of tensile stress to said test specimen increases the compressive engagement of said grip means with said test specimen, the improvement comprising,
said grip means being supported on said grip bars by threaded retainers passing through said grip bars and said housing includes aperture means for access to said threaded retainers.

12. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a cavity communicating with said receiving end for receiving one end of a test specimen within said housing, a pair of opposed wedging surfaces for slidably supporting jaw members within said cavity, said opposed wedging surfaces converging toward said receiving end of said housing, and a pair of opposed jaw members slidable over said wedging surfaces and including opposed grip means adapted to compressively engage opposed surfaces of a test specimen received within said cavity, the improvement comprising,
each of said opposed grip means being constructed and arranged to extend transversely of said jaw members a distance greater than the width of said jaw members.

13. Test specimen grip apparatus according to claim 12 which further includes fluid actuation means operatively connected to said jaw members to selectively slide said jaw members between an open position and a closed position.

14. Test specimen grip apparatus according to claim 13 which further includes locking means carried on said housing for locking said grip bars in a selected open position and wherein said grip means are supported on said grip bars by threaded retainers passing through said grip bars and said housing includes aperture means for access to said threaded retainers.

15. Test specimen grip apparatus according to claim 12 which further includes locking means carried on said housing for locking said jaw members in a selected open position.

16. Test specimen grip apparatus according to claim 12 wherein said grip means are supported on said jaw members by threaded retainers passing through said grip bars and said housing includes aperture means for access to said threaded retainers.

17. Test specimen grip apparatus according to claim 12 which further includes each of said opposed grip means carrying clamping means on its transverse extremities.

18. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a cavity communicating with said receiving end for receiving one end of a test specimen within said housing, a pair of opposed wedging surfaces for slidably supporting jaw members within said cavity, said opposed wedging surfaces converging toward said receiving end of said housing, and a pair of opposed jaw members slidable over said wedging surfaces and including opposed grip means adapted to compressively engage opposed surfaces of a test specimen received within said cavity.

The improvement comprising,
fluid actuation means mounted on the exterior of said housing and operatively connected to said grip bars at a location outside of said housing to selectively slide said grip bars between an open position pg,34 closed position.

19. Test specimen grip apparatus according to claim 18 which further includes locking means carried on said housing for locking said grip bars in a selected open position.

20. Test specimen grip apparatus according to claim 18 wherein said grip means are supported on said grip bars by threaded retainers passing through said grip bars and said housing includes aperture means for access to said threaded retainers.

21. The test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a cavity communicating with said receiving end for receiving one end of a test specimen within said housing, a pair of opposed wedging surfaces for slidably supporting jaw members within said cavity, said opposed wedging surfaces converging toward said receiving end of said housing, and a pair of opposed jaw members slidable over said wedging surfaces and including opposed grip means adapted to compressively engage opposed surfaces of a test specimen received within said cavity, the improvement comprising,
locking means carried on said housing for locking said grip bars in a selected open position.

22. Test specimen grip apparatus according to claim 21 wherein said grip means are supported on said grip bars by threaded retainers passing through said grip bars and said housing includes aperture means for access to said threaded retainers.

23. In test specimen grip apparatus for use with tensile stress testing apparatus wherein said grip apparatus includes a housing having a connecting end adapted for securing said housing to said tensile stress testing apparatus, a test specimen receiving end opposite said connecting end of said housing, a cavity communicating with said receiving end for receiving one end of a test specimen within said housing, a pair of opposed wedging surfaces for slidably supporting jaw members within said cavity, said opposed wedging surfaces converging toward said receiving end of said housing, and a pair of opposed jaw members slidable over said wedging surfaces and including opposed grip means adapted to compressively engage opposed surfaces of a test specimen received within said housing, the improvement comprising,
said grip means being supported on said grip bars by threaded retainers passing through said grip bars and said housing includes apertures means for access to said threaded retainers.

* * * * *

UNITED STATES PATENT AND TRADEMARK OFFICE
CERTIFICATE OF CORRECTION

PATENT NO. : 4,888,995
DATED : December 26, 1989
INVENTOR(S) : John M. Curtis

It is certified that error appears in the above—identified patent and that said Letters Patent is hereby corrected as shown below:

Column 9, line 10, "grip bars" should read -- jaw members --.
, line 12, "grip bars" should read -- jaw members --.
, line 13, "grip bars" should read -- jaw members --.
, line 22, "grip bars" should read -- jaw members --.
, line 46, "grip bars" should read -- jaw members --.
, line 48, "grip bars" should read -- jaw members --.
, line 48, "pg, 34" should read -- and a --.
Column 10, line 1, "grip bars" should read -- jaw members --.
, lines 4 and 5, "grip bars" should read -- jaw members --.
, lines 5 and 6, "grip bars" should read -- jaw members --.
, line 25, "grip bars" should read -- jaw members --.
, lines 27 and 28, "grip bars" should read -- jaw members --.
, lines 28 and 29, "grip bars" should read -- jaw members --.
, line 47, "grip bars" should read -- jaw members --.
, line 48, "grip bars" should read -- jaw members --.

Signed and Sealed this

Eleventh Day of December, 1990

Attest:

HARRY F. MANBECK, JR.

*Attesting Officer*       *Commissioner of Patents and Trademarks*